US00PP21627P2

(12) United States Plant Patent
Bernuetz

(10) Patent No.: US PP21,627 P2
(45) Date of Patent: Jan. 11, 2011

(54) ***BRACHYSCOME* PLANT NAMED 'BONBRAPI'**
(50) Latin Name: *Brachyscome×hybrida*
Varietal Denomination: Bonbrapi

(75) Inventor: Andrew Bernuetz, Silverdale (AU)
(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 12/587,459

(22) Filed: Oct. 7, 2009

(51) Int. Cl.
*A01H 5/00* (2006.01)
(52) U.S. Cl. ..... Plt./411

(58) Field of Classification Search ..... Plt./411
See application file for complete search history.

*Primary Examiner*—Kent L Bell
(74) *Attorney, Agent, or Firm*—C. A. Whealy

(57) ABSTRACT

A new and distinct cultivar of *Brachyscome* plant named 'Bonbrapi', characterized by its upright and outwardly spreading plant habit; freely branching growth habit; brown-colored stems and purple-tinted developing leaves; numerous large inflorescences positioned above the foliage; dark pink-colored ray florets; and good postproduction longevity and garden performance.

1 Drawing Sheet

Botanical designation: *Brachyscome×hybrida.*
Cultivar denomination: 'Bonbrapi'.

BACKGROUND OF THE INVENTION

The present invention relates to a new and distinct cultivar of *Brachyscome* plant, botanically known as *Brachyscome× hybrida* and hereinafter referred to by the name 'Bonbrapi'.

The new *Brachyscome* plant is a product of a controlled breeding program conducted by the Inventor in Yellow Rock, New South Wales, Australia. The objective of the breeding program is to create new mounding *Brachyscome* plants with unique and attractive ray floret color.

The new *Brachyscome* plant originated from a cross-pollination in Yellow Rock, New South Wales, Australia, of a proprietary selection of *Brachyscome formosa* identified as code number 00-126.2, not patented, as the female, or seed, parent with a proprietary selection of *Brachyscome×hybrida* identified as code number 00-52, not patented, as the male, or pollen, parent in September, 2004. The new *Brachyscome* plant was discovered and selected by the Inventor as a single flowering plant from within the progeny of the stated cross-pollination in a controlled environment in Yellow Rock, New South Wales, Australia in July, 2005.

Asexual reproduction of the new *Brachyscome* plant by vegetative cuttings in a controlled environment in Yellow Rock, New South Wales, Australia since August, 2005, has shown that the unique features of this new *Brachyscome* plant are stable and reproduced true to type in successive generations.

SUMMARY OF THE INVENTION

Plants of the new *Brachyscome* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Bonbrapi'.

These characteristics in combination distinguish 'Bonbrapi' as a new and distinct cultivar of *Brachyscome:*

1. Upright and outwardly spreading plant habit.
2. Freely branching growth habit.
3. Brown-colored stems and purple-tinted developing leaves.
4. Numerous large inflorescences positioned above the foliage.
5. Dark pink-colored ray florets.
6. Good postproduction longevity and garden performance.

Plants of the new *Brachyscome* differ from plants of the female parent selection primarily in the following characteristics:

1. Plants of the new *Brachyscome* have smaller inflorescences than plants of the female parent selection.
2. Plants of the new *Brachyscome* have lighter-colored ray florets than plants of the female parent selection.

Plants of the new *Brachyscome* differ from plants of the male parent selection primarily in the following characteristics:

1. Plants of the new *Brachyscome* and the male parent selection differ in developing leaf color as plants of the male parent selection have green-colored developing leaves.
2. Plants of the new *Brachyscome* have larger inflorescences than plants of the male parent selection.

Plants of the new *Brachyscome* can also be compared to plants of the *Brachyscome angustifolia* 'Billabong Mauve Delight', disclosed in U.S. Plant Pat. No. 10,889. In side-by-side comparisons conducted in Yellow Rock, New South Wales, Australia, plants of the new *Brachyscome* differed from plants of 'Billabong Mauve Delight' in the following characteristics:

1. Plants of the new *Brachyscome* were more compact than plants of 'Billabong Mauve Delight'.
2. Plants of the new *Brachyscome* had longer internodes than plants of 'Billabong Mauve Delight'.
3. Plants of the new *Brachyscome* and 'Billabong Mauve Delight' differed in stem and developing leaf color as plants of 'Billabong Mauve Delight' had green-colored stems and developing leaves.

4. Plants of the new *Brachyscome* had larger leaves than plants of 'Billabong Mauve Delight'.
5. Plants of the new *Brachyscome* had larger inflorescences than plants of 'Billabong Mauve Delight'.
6. Plants of the new *Brachyscome* and 'Billabong Mauve Delight' differed in ray floret color as plants of 'Billabong Mauve Delight' had violet-colored ray florets.

BRIEF DESCRIPTION OF THE PHOTOGRAPHS

The accompanying colored photographs illustrate the overall appearance of the new *Brachyscome* plant, showing the colors as true as it is reasonably possible to obtain in colored reproductions of this type. Colors in the photographs may differ slightly from the color values cited in the detailed botanical description which accurately describe the colors of the new *Brachyscome* plant.

The photograph at the top of the sheet comprises a side perspective view of a typical flowering plant of 'Bonbrapi' grown in a container.

The photograph at the bottom of the sheet is a close-up view of typical flowering plants of 'Bonbrapi'.

DETAILED BOTANICAL DESCRIPTION

The aforementioned photographs and following observations, measurements and values describe plants grown in 15-cm containers in Higashiomi, Shiga, Japan, under commercial practice during the early summer in an outdoor nursery with day temperatures ranging from 15° C. to 30° C. and night temperatures ranging from 8° C. to 20° C. Plants were four and five months old when the description and photographs, respectively, were taken. In the following description, color references are made to The Royal Horticultural Society Colour Chart, 2001 Edition, except where general terms of ordinary dictionary significance are used.

Botanical classification: *Brachyscome×hybrida* 'Bonbrapi'.

Parentage:

*Female, or seed, parent.*—Proprietary selection of *Brachyscome formosa* identified as code number 00-126.2, not patented.

*Male, or pollen, parent.*—Proprietary selection of *Brachyscome×hybrida* identified as code number 00-52, not patented.

Propagation:

*Type.*—By vegetative cuttings.

*Time to initiate roots, summer.*—About seven days at temperatures of 20° C. to 25° C.

*Time to initiate roots, winter.*—About ten days at temperatures of 15° C. to 20° C.

*Time to produce a rooted young plant, summer.*—About three weeks at temperatures of 20° C. to 25° C.

*Time to produce a rooted young plant, winter.*—About four weeks at temperatures of 15° C. to 20° C.

*Root description.*—Fibrous; white in color.

*Rooting habit.*—Freely branching; moderately dense.

Plant description:

*Plant form and growth habit.*—Upright and outwardly spreading plant habit; moderately vigorous growth habit; freely branching growth habit with about 70 lateral branches per plant; pinching enhances lateral branch development.

*Plant height.*—About 18.4 cm.

*Plant width (spread).*—About 34.2 cm.

*Lateral branches.*—Length: About 12.7 cm. Diameter: About 1.5 mm. Internode length: About 3.3 cm. Strength: Moderately strong. Aspect: Upright to outward. Texture: Smooth, glabrous. Color: Between N200A and 200B.

Foliage description:

*Arrangement.*—Alternate, simple; sessile.

*Length.*—About 3.8 cm.

*Width.*—About 2.1 cm.

*Shape.*—Obovate.

*Apex.*—Acute to somewhat obtuse.

*Base.*—Attenuate.

*Margin.*—Lobed.

*Texture, upper and lower surfaces.*—Smooth, glabrous.

*Venation pattern.*—Pinnate, reticulate.

*Color.*—Developing leaves, upper surface: Close to N189A tinted with close to 187A. Developing leaves, lower surface: Close to N187B. Fully expanded leaves, upper surface: Close to 189A; venation, close to 138A. Fully expanded leaves, lower surface: Close to 191A tinted with close to 187A; venation, close to N199A.

Inflorescence description:

*Appearance and habit.*—Single composite inflorescence form with ray and disc florets arranged acropetally on a capitulum; inflorescences borne above the foliage; uniform and freely flowering habit with about 26 open inflorescences per plant at a time; inflorescences face mostly upright.

*Fragrance.*—None detected.

*Flowering season.*—Plants flower from spring through autumn in Japan; flowering continuous during this period; early flowering habit, plants begin flowering about 35 days after planting.

*Inflorescence longevity.*—Inflorescences last about two to three weeks on the plant; inflorescences persistent.

*Inflorescence bud.*—Height: About 6.4 mm. Diameter: About 4.9 mm. Shape: Ovoid. Color: Close to 145C.

*Inflorescence size.*—Diameter: About 3.6 cm. Height: About 8 mm. Diameter of disc: About 6.6 mm.

*Ray florets.*—Quantity/arrangement: About 21 to 26 in a single whorl. Length: About 14.2 mm. Width: About 3 mm. Shape: Lanceolate. Apex: Obtuse. Base: Obtuse. Margin: Entire. Texture, upper and lower surfaces: Smooth, glabrous. Color: When opening, upper surface: Close to N78B. When opening, lower surface: Close to 65C; towards the base, close to 71B. Fully opened, upper surface: Close to N78C. Fully opened, lower surface: Close to 75B; towards the base, close to 72B.

*Disc florets.*—Quantity/arrangement: About 60 massed at center of receptacle. Shape: Tubular, elongated; five-lobed. Apex: Acute. Length: About 6.1 mm. Width: About 2.3 mm. Texture: Smooth, glabrous. Color, immature: Close to 146A. Color, mature: Close to 1B.

*Involucral bracts.*—Quantity/arrangement: About 18; bracts imbricate. Length: About 4.2 mm. Width: About 0.9 mm. Shape: Elliptic to oblong. Apex: Acute. Base: Truncate. Margin: Entire, ciliate. Texture, upper and lower surfaces: Smooth, glabrous. Color, upper surface: Close to 200B. Color, lower surface: Close to 137A to 137C.

*Peduncles.*—Length: About 7.6 cm. Diameter: About 1 mm. Strength: Moderately strong. Texture: Smooth, glabrous. Color: Between N200A and 200B.

*Reproductive organs.*—Androecium: Present on disc florets only. Stamen length: About 1 mm. Anther length: Less than 1 mm. Anther shape: Lanceolate. Anther color: Close to 13C. Pollen amount: Moderate. Pollen color: Close to 13C. Gynoecium: Present on ray and disc florets. Pistil length: About 4.1 mm. Stigma shape: Bi-lobed. Stigma color: Close to 13C. Ovary color: Close to 145C.

*Seeds/fruits.*—Seed and fruit development has not been observed on plants of the new *Brachyscome.*

Disease/pest resistance: Plants of the new *Brachyscome* have not been observed to be resistant to pathogens and pests common to *Brachyscomes.*

Garden performance: Plants of the new *Brachyscome* have been observed to have good garden performance and tolerate rain, wind and temperatures ranging from about 0° C. to about 40° C.

It is claimed:

1. A new and distinct *Brachyscome* plant named 'Bonbrapi' as illustrated and described.

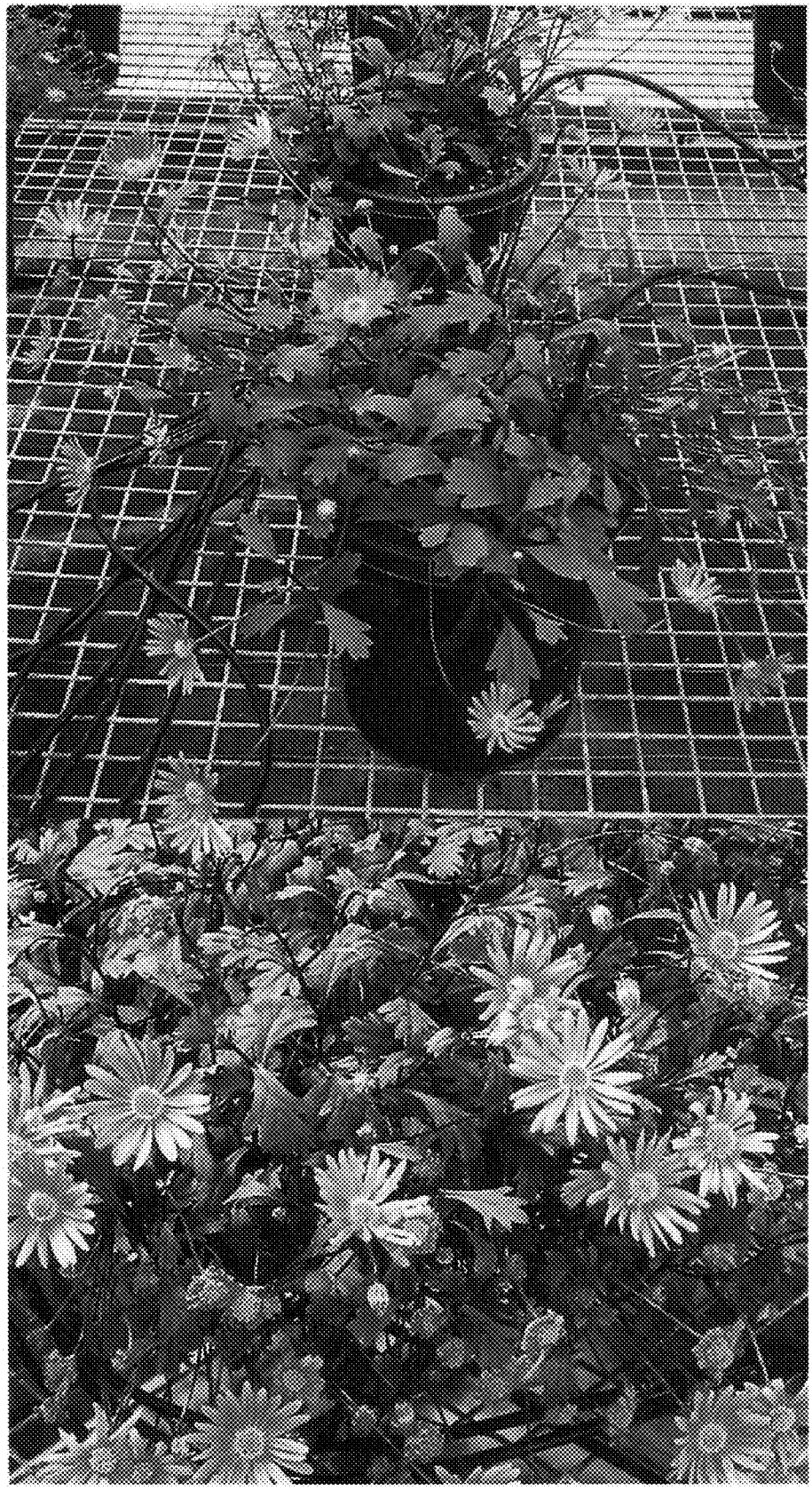

* * * * *